(12) United States Patent
Maspoli et al.

(10) Patent No.: US 12,727,998 B2
(45) Date of Patent: Sep. 8, 2026

(54) CATHETER DEVICE COMPRISING AN OVERSTROKE STOP MECHANISM AND/OR A RE-SHEATHING LIMIT MECHANISM

(71) Applicant: BIOTRONIK AG, Buelach (CH)

(72) Inventors: Peter Maspoli, Buelach (CH); Cassie Strauss, Buelach (CH); Markus Hepke, Waltrop (CH)

(73) Assignee: BIOTRONIK AG, Buelach (CH)

(*) Notice: Subject to any disclaimer, the term of this patent is extended or adjusted under 35 U.S.C. 154(b) by 1129 days.

(21) Appl. No.: 17/783,102

(22) PCT Filed: Jan. 15, 2021

(86) PCT No.: PCT/EP2021/050792
§ 371 (c)(1),
(2) Date: Jun. 7, 2022

(87) PCT Pub. No.: WO2021/151690
PCT Pub. Date: Aug. 5, 2021

(65) Prior Publication Data

US 2023/0017331 A1 Jan. 19, 2023

(30) Foreign Application Priority Data

Jan. 27, 2020 (EP) .................................... 20153792

(51) Int. Cl.

| | |
|---|---|
| ***A61F 2/24*** | (2006.01) |
| ***A61F 2/95*** | (2013.01) |
| ***A61F 2/966*** | (2013.01) |

(52) U.S. Cl.
CPC .......... *A61F 2/2436* (2013.01); *A61F 2/9517* (2020.05); *A61F 2002/9665* (2013.01)

(58) Field of Classification Search
CPC .................. A61F 2/2436; A61F 2/9517; A61F 2002/9665; A61F 2002/9505; A61F 2/966; A61F 2002/9534
See application file for complete search history.

(56) References Cited

U.S. PATENT DOCUMENTS

| | | | | |
|---|---|---|---|---|
| 9,717,595 | B2 * | 8/2017 | Costello | A61F 2/2436 |
| 2014/0031922 | A1 * | 1/2014 | Duffy | A61F 2/966 623/2.11 |
| 2015/0305902 | A1 * | 10/2015 | Argentine | A61F 2/966 623/1.12 |

FOREIGN PATENT DOCUMENTS

| | | | |
|---|---|---|---|
| WO | 0149215 | A2 | 7/2001 |
| WO | 03068302 | A2 | 8/2003 |
| WO | 2005067819 | A1 | 7/2005 |

OTHER PUBLICATIONS

International Search Report from the corresponding International Patent Application No. PCT/EP2021/050792, dated Mar. 8, 2021.

* cited by examiner

*Primary Examiner* — Thomas C Barrett
*Assistant Examiner* — Jose H. Trevino, III
(74) *Attorney, Agent, or Firm* — Greer, Burns & Crain, Ltd.; Steven P. Fallon

(57) ABSTRACT

A catheter device for implanting a medical implant includes an actuating element configured to move with a capsule of the catheter device and to be manually operated to bring the actuating element from a first state to a second state. A first and/or second stop is included in the catheter device. The first stop is configured to limit a movement of the actuating element and therewith of the capsule in a first direction, e.g. proximal direction (P), when the actuating element is in the first state. The second stop is configured to limit a movement of the actuating element and therewith of the capsule in a (Continued)

second direction, e.g. distal direction (D), when the actuating element is in the first state, so as to prevent pressing of the capsule against a catheter tip of the catheter device and/or against a capsule stop of the catheter device.

15 Claims, 11 Drawing Sheets

1
10
11
12
31
3
30
4
4a
32
8
x
P
D
5
51
130
52
53
54
51a
52a
(A-A)
510
52b
50
51b
520
A
7

1
11
10
12
31
3
30
4
32
4a
8
x
P
D 5
130
52
52b
52a
(A-A)
50
130
5
A
A 1
10
11
12
P
D
4
4a
31
3
30
2
32
8
x 5
130
52
52b
52a
50
(A-A)

A
A
6
7
130

91
6
133
9
5
7
83
82
130a
R1
R2
1
P
D
131
81
80
90
130
132
13
X 6
133
9
5
7
1
13
83
82
131
130
P
D

FIG. 11
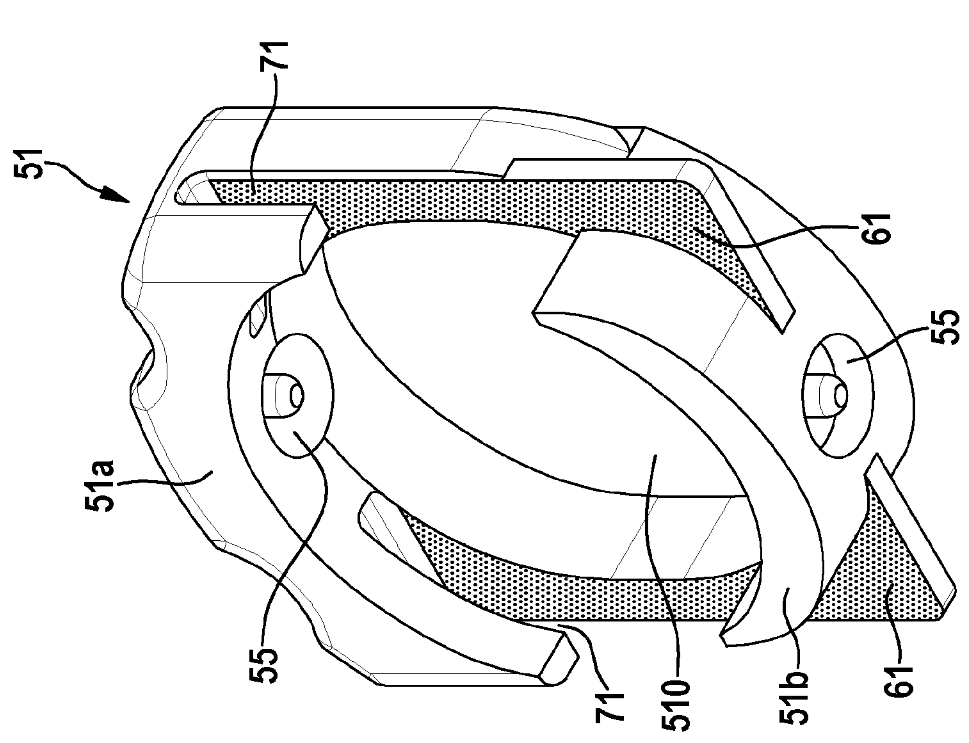
51
71
61
55
51a
55
71
510
51b
61
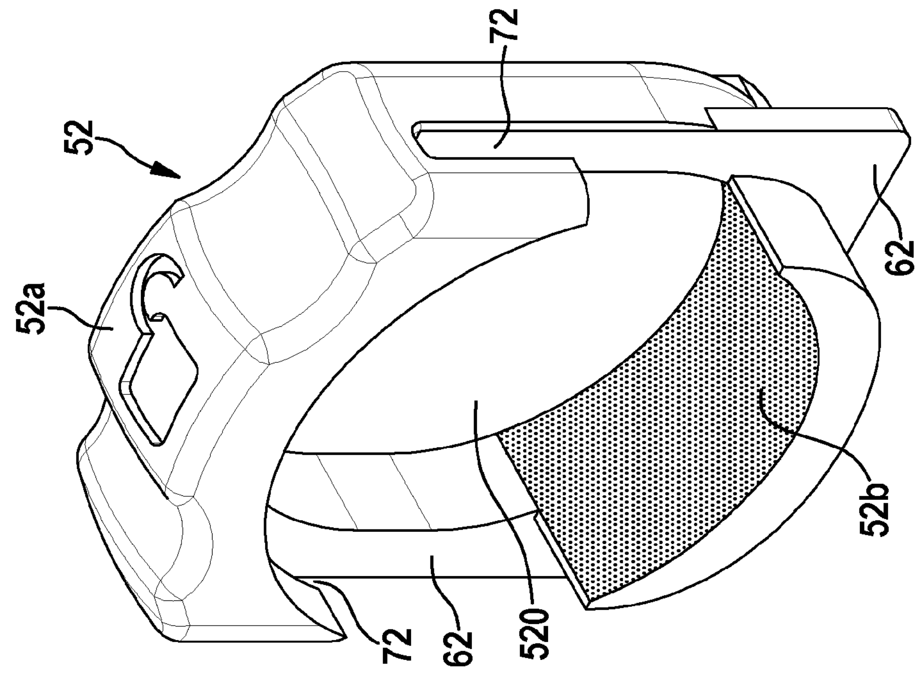
52
72
52a
62
52b
520
62
72

FIG. 12
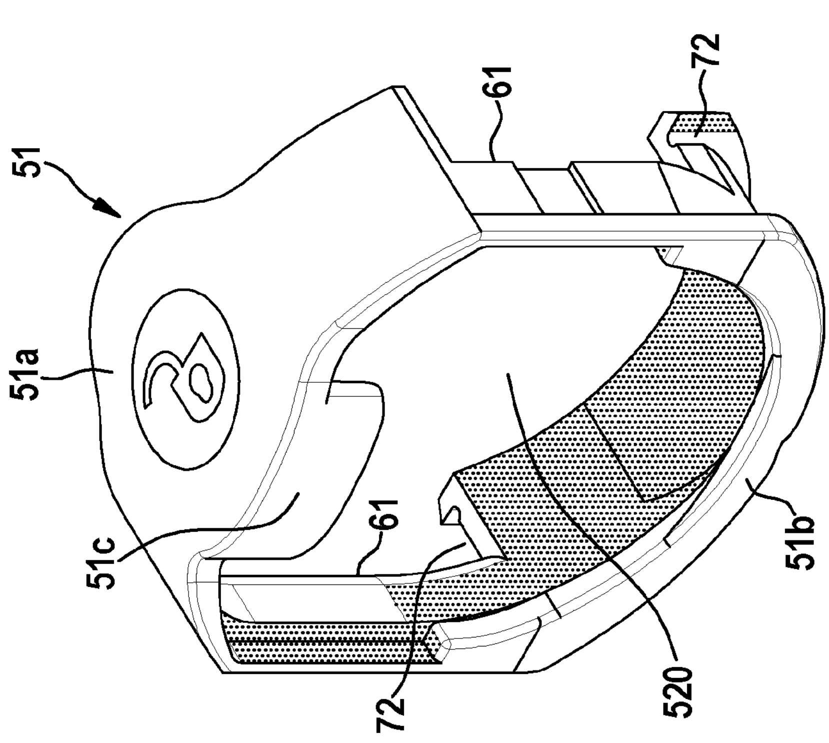
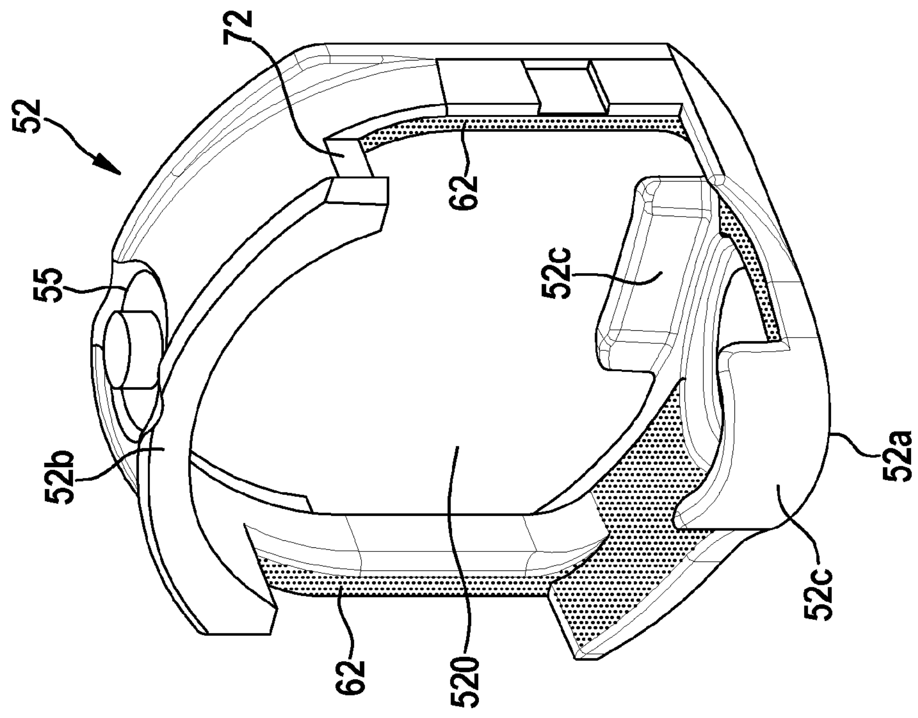

CATHETER DEVICE COMPRISING AN OVERSTROKE STOP MECHANISM AND/OR A RE-SHEATHING LIMIT MECHANISM

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2021/050792, which was filed Jan. 15, 2021, which application claimed priority from European Application Serial Number 20153792.5, which was filed Jan. 27, 2020.

FIELD OF THE INVENTION

A field of the invention is catheter devices used for implanting a medical implant, particularly a prosthetic heart valve such as an aortic prosthetic heart valve.

BACKGROUND

A typical catheter device usually includes a capsule for receiving the implant such as a self-expanding aortic prosthetic heart valve when the latter is in a collapsed/crimped state. The capsule covers the implant (e.g. a self-expanding aortic prosthetic heart valve) that is placed on a connector connected to an inner sheath/shaft of the catheter device while the capsule is connected to an outer sheath/shaft. Sliding of the outer sheath/shaft with respect to the inner sheath/shaft allows displacing the capsule with respect to the inner sheath/connector, so to allow the self-expanding medical implant to deploy and to release the implant from the connector. Particularly, a medical implant like a prosthetic heart valve such as an aortic prosthetic heart valve can be partially deployed and can be retracted into the capsule for the purpose of re-positioning the implant so that it is situated at a proper implantation site. Reinserting the medical implant into the capsule is commonly termed "re-sheathing". However, re-sheathing is only possible in case the medical implant is still connected to the catheter device.

For instance, moving the capsule in the proximal direction too far may cause unwanted release of the medical implant, while moving the capsule to far in the distal direction may introduce an overstroke into coaxial sheaths/shafts of the catheter device which can increase sheath/shaft stiffness and/or cause component misalignment (e.g. capsule moves over a catheter tip and e.g. the crossing profile changes). Also, in certain instances a component compression may occur.

In view of the above, the same applies if the catheter device has an alternative arrangement, meaning that moving the capsule in the distal direction too far may cause unwanted release of the medical implant, while moving the capsule too far in the proximal direction may introduce an overstroke into coaxial sheaths/shafts of the catheter device which can increase sheath/shaft stiffness and/or cause component misalignment. Also, in certain instances a component compression may occur in such scenario as well.

Therefore, a problem to be solved by the present invention is to provide a catheter device that can prevent the occurrence of at least one of the above-stated difficulties, and ideally allows preventing unwanted release of the implant, so to allow controlled re-sheathing as well avoiding introduction of said "overstroke" and/or misalignment of catheter device components.

SUMMARY OF THE INVENTION

A catheter device for implanting a medical implant includes an actuating element configured to move with a capsule of the catheter device and to be manually operated to bring the actuating element from a first state to a second state. A first and/or second stop is included in the catheter device. The first stop is configured to limit a movement of the actuating element and therewith of the capsule in a first direction, e.g. proximal direction (P), when the actuating element is in the first state. The second stop is configured to limit a movement of the actuating element and therewith of the capsule in a second direction, e.g. distal direction (D), when the actuating element is in the first state, so as to prevent pressing of the capsule against a catheter tip of the catheter device and/or against a capsule stop of the catheter device.

BRIEF DESCRIPTION OF THE DRAWINGS

In the following embodiments of the present invention as well as further features and advantages of the present invention are described with reference to the drawings, wherein:

FIGS. 11A-11B show a further embodiment of an actuating element of the catheter device according to the present invention including increased guiding surfaces; and FIGS. 12A-12B show a further embodiment of an actuating element of the catheter device according to the present invention including guiding surfaces (cf. emphasized portions therein).

DETAILED DESCRIPTION OF THE PREFERRED EMBODIMENTS

Figure 1:
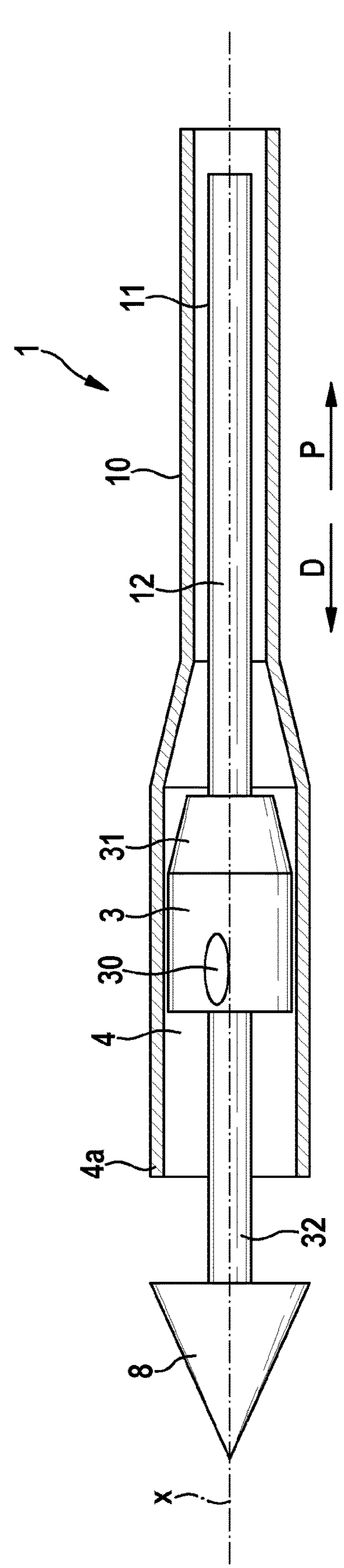
FIGS. 1A-1C show a schematic view of an embodiment of a catheter system according to the present invention including a first stop and an actuating element for forming an overstroke limit, wherein in FIG. 1 the overstroke limit is not yet reached, allowing free movement between inner and outer sheath of the catheter device.
Figure 1:
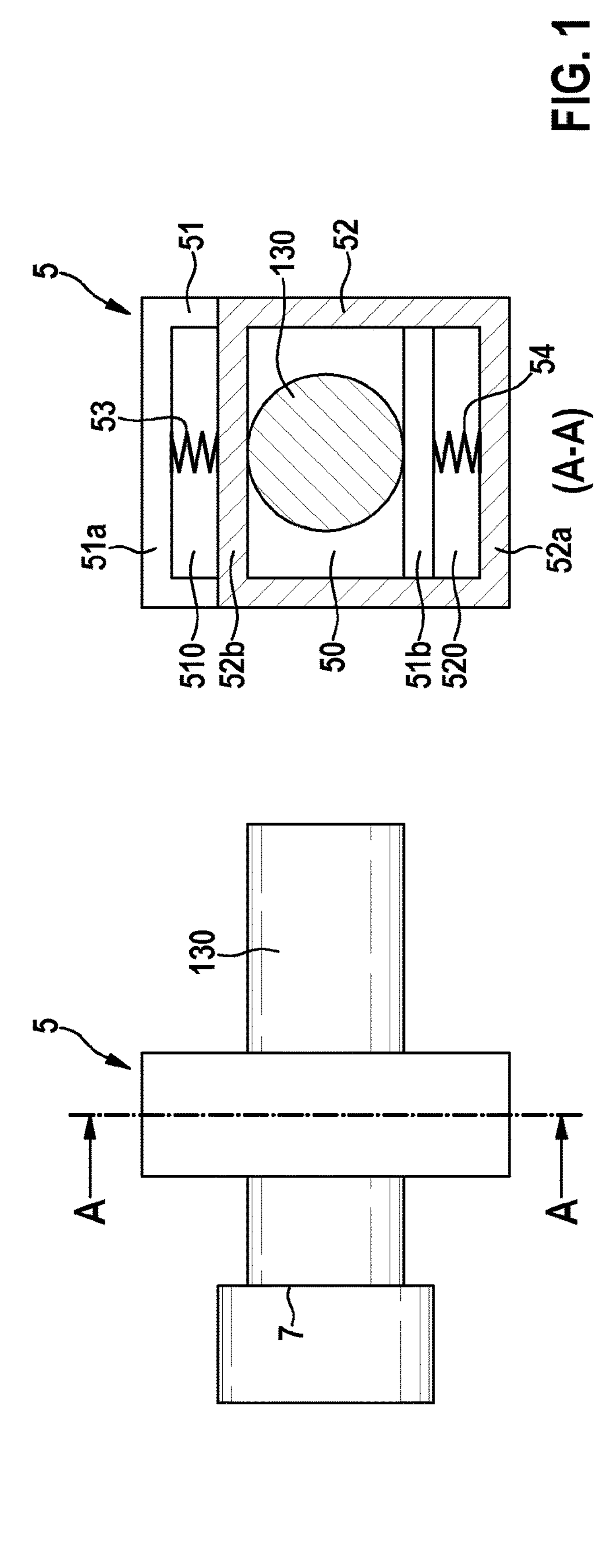

A preferred catheter device includes an actuating element configured to move with the capsule and to be manually operated to bring the actuating element from a first state to a second state. A first stop is configured to limit a movement of the actuating element and therewith of the capsule in the second direction, e.g. distal direction, when the actuating element is in the first state, so as to prevent pressing of the capsule against a catheter tip of the catheter device and/or against a capsule stop of the catheter device, and configured to allow movement of the actuating element past the first stop when the actuating element is in the second state, so as to press the capsule against the catheter tip and/or against the capsule stop. A second stop is configured to limit a movement of the actuating element and therewith of the capsule in the first direction, e.g. proximal direction, when the actuating element is in the first state, so as to prevent release of the medical implant from the connector, and configured to allow movement of the actuating element past the second stop when the actuating element is in the second state, so as to allow complete deployment and release of the medical implant from the connector.

Thus, the present invention provides in each case a defined limit which forces the user to consciously overcome the respective limit. In this way, the risk of an unwanted release or introduction of an overstroke into the system is essentially prevented. The catheter device according to the present invention can include only one of these stops or both stops.

With the context of the present invention, the first direction may be a distal direction whereas the second direction is the opposite, namely a proximal direction, or the first direction may be a proximal direction P and the second direction is the opposite, namely a distal direction.

Following the above, it is a general purpose of the invention to inter alia allow for an additional travel path of the catheter shaft system including the capsule, and thus also for the implant, if the catheter shaft system has warped as described above; e.g. during a resheathing.

Particularly, according to an embodiment, a symmetric button design may be employed which is integrated into the flux of force in combination with a hard stop coupled to coaxial sheaths/shafts of the catheter device. Such a concept as well as other embodiments described herein can be applied to an overstroke stop/limit mechanism as well as to a re-sheathing limit mechanism of the device as will be described in more detail below.

Throughout the text, the terms "sheath(s)" and "shaft(s)" may be used interchangeably. However, in certain instances and within the context of the present invention a "shaft" may be also referred as a "sheath" whereas a "sheath" not necessarily must be configured as a "shaft".

In the framework of the present invention, and thus relating to a catheter device/catheter system, the notion "distal" refers to a portion or components of the system that is remote from a handle of the catheter device or from the physician that operates the catheter device while the notion "proximal" refers to those portions or components that are closer to the handle or closer to the physician.

According to an embodiment of the catheter device, the catheter device further includes an outer sheath/shaft connected to the capsule, extending along a longitudinal axis of the catheter device and surrounding a lumen of the outer sheath/shaft, and an inner sheath/shaft extending along the longitudinal axis, wherein the inner sheath/shaft is arranged in the lumen of the outer sheath and is connected to the connector for supporting/holding the medical implant.

Further, according to an embodiment of the catheter device, the catheter device includes a handle for moving the capsule with respect to the medical implant, wherein the handle includes a handle core and a rotatable member arranged on the handle core, wherein the rotatable member is operatively connected to the capsule, particularly via the outer sheath/shaft, such that the capsule is moved in the first direction, e.g. proximal direction, and thereby gradually removed from the medical implant when the rotatable member is rotated in a first rotation direction, and such that the capsule is moved back in the second direction, e.g. distal direction, to re-sheath the medical implant when the rotatable member is rotated in an opposite second rotation direction.

According to an embodiment, the handle further includes a grip portion for manually holding the handle, wherein the grip portion is rigidly connected to the handle core.

Further, according to an embodiment of the catheter device, the actuating element includes a through-opening that includes a first diameter in the first state of the actuating element and a larger second diameter in the second state of the actuating element, wherein the handle core preferably extends through the through-opening.

According to an embodiment of the catheter device, the second stop is arranged on the handle core, wherein when the capsule is moved in the first direction, e.g. proximal direction, the actuating element is configured to hit the second stop when the actuating element is in the first state and allowed to move past the second stop in the first direction, e.g. proximal direction, when the actuating element is in the second state. This is due to the fact that in the first state the inner diameter is not large enough to allow the actuating element to pass the second stop, which is only possible when the actuating element is in the second state (i.e. includes the larger second diameter).

Furthermore, according to an embodiment of the catheter device, the capsule is operatively connected to the rotatable member such that the implant is in a partially deployed state when the actuating element hits the second stop and is re-sheathable by rotating the rotatable member in the second rotation direction, and such that the medical implant is completely deployed and released from the connector when the actuating element is moved past the second stop in the first direction, e.g. proximal direction.

Further, in an embodiment, the first stop is arranged on the handle core, wherein when the capsule is moved in the second direction, e.g. distal direction, the actuating element is configured to hit the first stop when the actuating element is in the first state, and allowed to move past the first stop in the second direction, e.g. distal direction, when the actuating element is in the second state.

Furthermore, in an embodiment, the capsule is operatively connected to the rotatable member such that a distal end of the capsule contacts the catheter tip of the catheter device and the capsule completely covers the medical implant when the actuating element hits the first stop (and when the medical implant is arranged on/connected to the connector), and such that the capsule is pressed against the catheter tip and/or against the capsule stop when the actuating element is moved past the first stop in the second direction, e.g. distal direction.

Furthermore, according to an embodiment of the catheter device, the actuating element includes a movable first member including a first opening, and a movable second member including a second opening, wherein the two movable members are arranged side-by-side, so that overlapping regions of the openings of the two movable members form the through-opening of the actuating element. Furthermore, particularly, each of the two movable members is configured to be manually moved from a first position to a second position, wherein, when the first and the second member reside in the respective first position, the actuating element is in the first state and the through-opening of the actuating element includes the first diameter, and wherein when the first and the second member reside in the respective second position, the actuating element is in the second state and the through-opening of the actuating element includes the larger second diameter.

Furthermore, according to an embodiment of the catheter device, each of the two movable members includes a first portion and an opposing second portion, wherein the respective first portion forms a manually pushable button, and wherein the two movable members are arranged such with respect to one another that the first portion of the first movable member faces the second portion of the second movable member, and such that the second portion of the first movable member faces the first portion of the second movable member.

Furthermore, according to an embodiment of the catheter device, the catheter device includes a first spring, for example a coil spring, arranged between the first portion of the first movable member and the second portion of the second movable member, and wherein the catheter device includes a second spring, for example a coil spring, arranged between the first portion of the second movable member and the second portion of the first movable member, so that the two first portions (pushable buttons) can be manually pushed towards one another to move the movable members from the first positions to their second positions against a restoring force generated by the first and the second spring.

Furthermore, according to an embodiment of the catheter device, the first portion of the first movable member includes a recess (for example a circular groove) receiving a first end of the first spring, and wherein the second portion of the second movable member includes a recess (for example a circular groove) receiving a second end of the first spring. Likewise, in an embodiment, the first portion of the second movable member includes a recess (for example a circular groove) receiving a first end of the second spring, and wherein the second portion of the first movable member includes a recess (for example a circular groove) receiving a second end of the second spring. Particularly, in case coil springs are used for the first and the second spring, circular grooves are advantageous for holding the ends of the respective spring (for example in a form-fitting manner).

Furthermore, according to an embodiment of the catheter device, each of the two movable members includes at least one flat guiding surface, wherein the at least one flat guiding surface of the first movable member is configured to slide along the at least one flat guiding surface of the second movable member when the two movable members are moved from their respective first position to their respective second position.

Furthermore, according to an embodiment, each of the two movable members includes at least one recess (e.g. a slot) into which the at least one flat guiding surface of the other movable member engages, particularly so as to prevent separation of the two movable members when they slide along one another.

Furthermore, according to an embodiment of the catheter device, the capsule is connected to the rotatable member via the outer sheath/shaft, wherein the rotatable member includes a first inner thread engaging with an outer thread formed on the handle core such that the rotatable member and therewith the capsule is moved in the first direction, e.g. proximal direction, when the rotatable member is rotated in the first rotation direction and such that the rotatable member and therewith the capsule is moved in the second direction, e.g. distal direction, when it is rotated in the second rotation direction.

Furthermore, according to an embodiment, the catheter device includes a traveler to which the inner sheath is connected (which in turn is connected to the connector), wherein the traveler is arranged in a lumen of the handle core and includes an outer thread configured to engage with a second inner thread of the rotatable member such that the traveler and therewith the connector (medical implant) is moved in the second direction, e.g. distal direction, when the rotatable member is rotated in the first rotation direction and such that the traveler and therewith the connector (medical implant) is moved in the first direction, e.g. proximal direction. when the rotatable member is rotated in the second rotation direction.

Furthermore, according to a preferred embodiment, the medical implant is a prosthetic heart valve, e.g. an aortic prosthetic heart valve, that can include said self-expanding stent for carrying an artificial valve. Furthermore, the valve can include valve leaflets (for example three valve leaflets) that can be connected to the stent. The valve leaflets can be formed out of a biological tissue.

Thus, in an embodiment, the prosthetic heart valve is configured for replacing an aortic heart valve. Preferably, the catheter device is a TAVI/TAVR catheter device, i.e. a catheter device for transcatheter aortic valve implantation (TAVI) or transcatheter aortic valve replacement (TAVR), respectively. Here, the catheter device can be configured to deliver the prosthetic heart valve transfemorally (in the upper leg) or transapically (through the wall of the heart) or subclavian (beneath the collar bone) or direct aortic (through a minimally invasive surgical incision into the aorta) or transcavally (from a temporary hole in the aorta near the belly button through a vein in the upper leg).

Figures 7A, 7B, 7C:
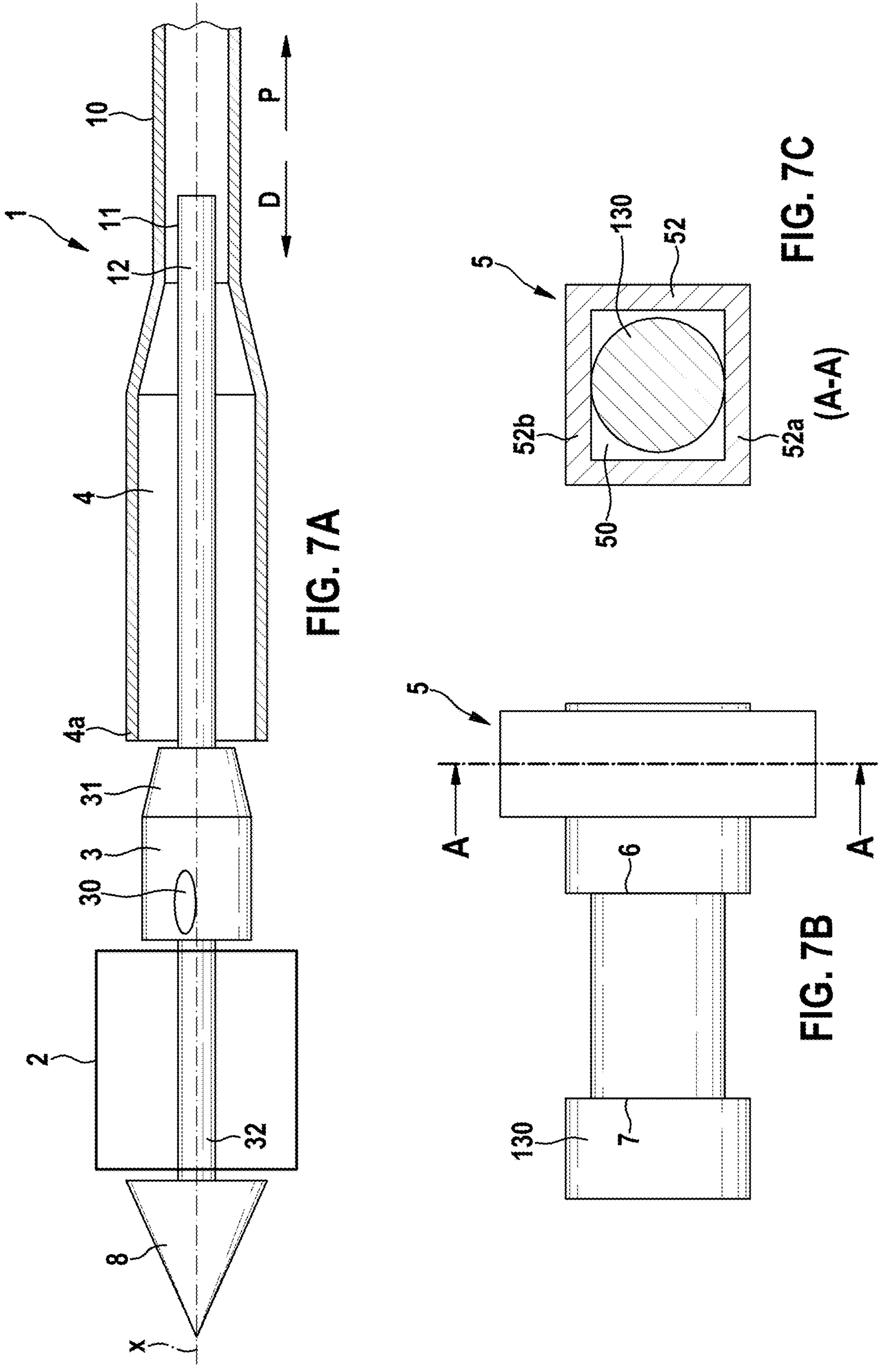
FIGS. 7A-7C show the embodiment of FIG. 6, wherein the re-sheathing limit is overcome, so that the sheaths can be moved until full medical implant release is accomplished.
Figure 7D:
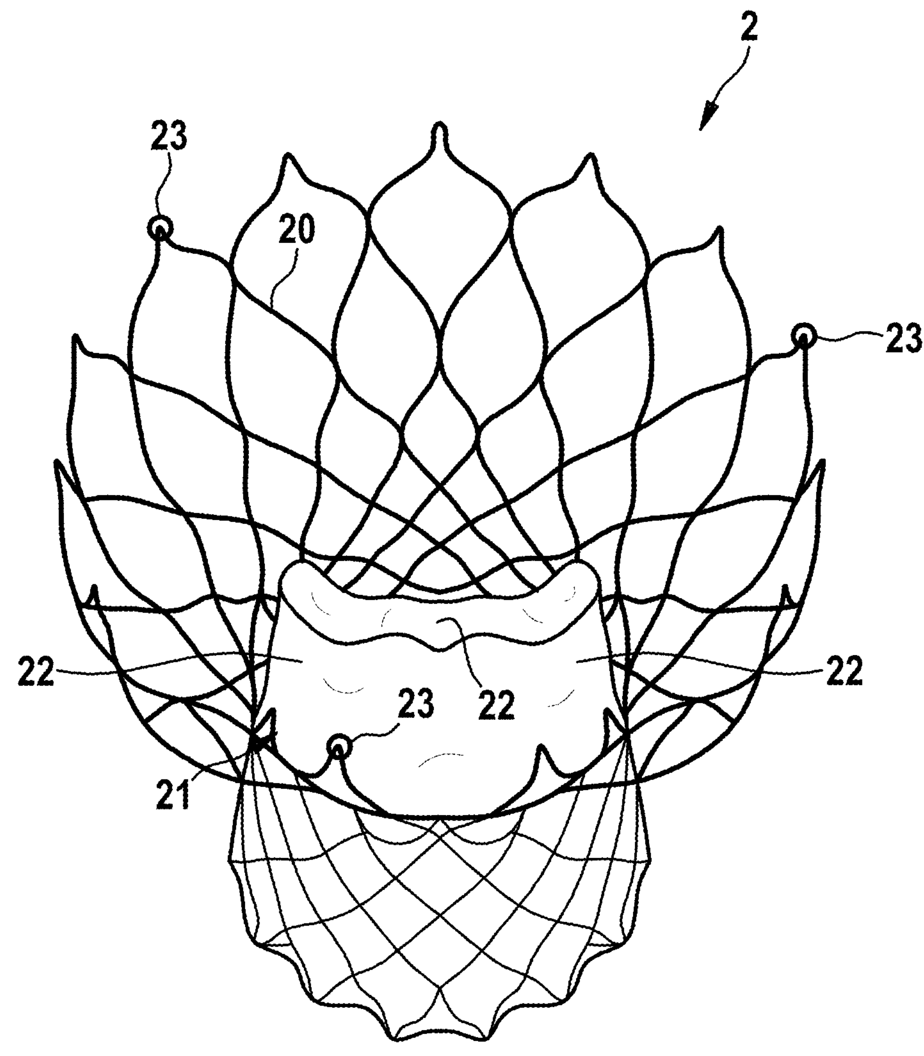
FIG. 7D shows an embodiment of a medical implant in form of an exemplary aortic prosthetic heart valve that can be implanted with the catheter device according to the present invention.

FIGS. 1A-1C show an embodiment of a catheter device 1 according to the present invention for implanting a medical implant 2 (for example an aortic prosthetic heart valve 2 as shown in FIG. 7D). The catheter device 1 further includes a connector 3 for holding the medical implant 2 (not shown in FIGS. 1A-1C), and a capsule 4 configured to cover the medical implant 2 when the medical implant 2 is arranged on the connector 3 and to thereby prevent release of the medical implant from the connector 3, wherein the capsule 4 is exemplarily movable in a proximal direction P with respect to the medical implant 2 for deploying the medical implant 2 and for releasing the medical implant 2 from the connector 3, and wherein the capsule 4 is exemplarily movable in a distal direction D for re-sheathing the medical implant 2 before it is released from the connector 3.

The catheter device 1 preferably includes an outer sheath/shaft 10 having a distal end that is connected to the capsule 4. The outer sheath/shaft 10 extends along a longitudinal axis x of the catheter device 1 and surrounds a lumen 11 of the outer sheath/shaft 10. The catheter device 1 preferably further include an inner sheath/shaft 12 extending along the longitudinal axis x, wherein the inner sheath/shaft 12 is arranged in the lumen 11 of the outer sheath/shaft and connected to the connector 3. The connector 3 in turn can be connected to the catheter tip 8 via a tubing 32. Particularly, the catheter tip 8 can include an opening formed in a distal end of the catheter tip 8, so that a guidewire for guiding the catheter device 1 during implantation of the implant 2 can extend in a guidewire of the inner sheath 12 and the tubing 32 and exit the guidewire lumen via said opening of the catheter tip 8. Particularly, the coaxial sheaths/shafts 10, 12 are flexible so that they can follow a curved course of a blood vessel via which the implant is transported to an implantation site.

Furthermore, the catheter device 1 includes an actuating element 5 configured to move with the capsule 4 and to be manually operated to bring the actuating element 5 from a first state to a second state, and a first stop 7 configured to limit a movement of the actuating element 5 and therewith of the capsule 4 exemplarily in the distal direction D when the actuating element 5 is in the first state, so as to prevent pressing of the capsule 4 against a catheter tip 8 of the catheter device 1 and/or against a capsule stop 31 of the catheter device 1. Furthermore, the first stop 7 is configured to allow movement of the actuating element 5 past the first stop 7 in the distal direction D when the actuating element 5 is in the second state, so as to press the capsule 4 against the catheter tip 8 and/or against the capsule stop 31 which introduces a load into the coaxial sheaths 10, 12.

The first stop 7 thus defines an overstroke limit when inner and outer sheath 10, 12 are in a defined position with respect to each other.

Figure 2:
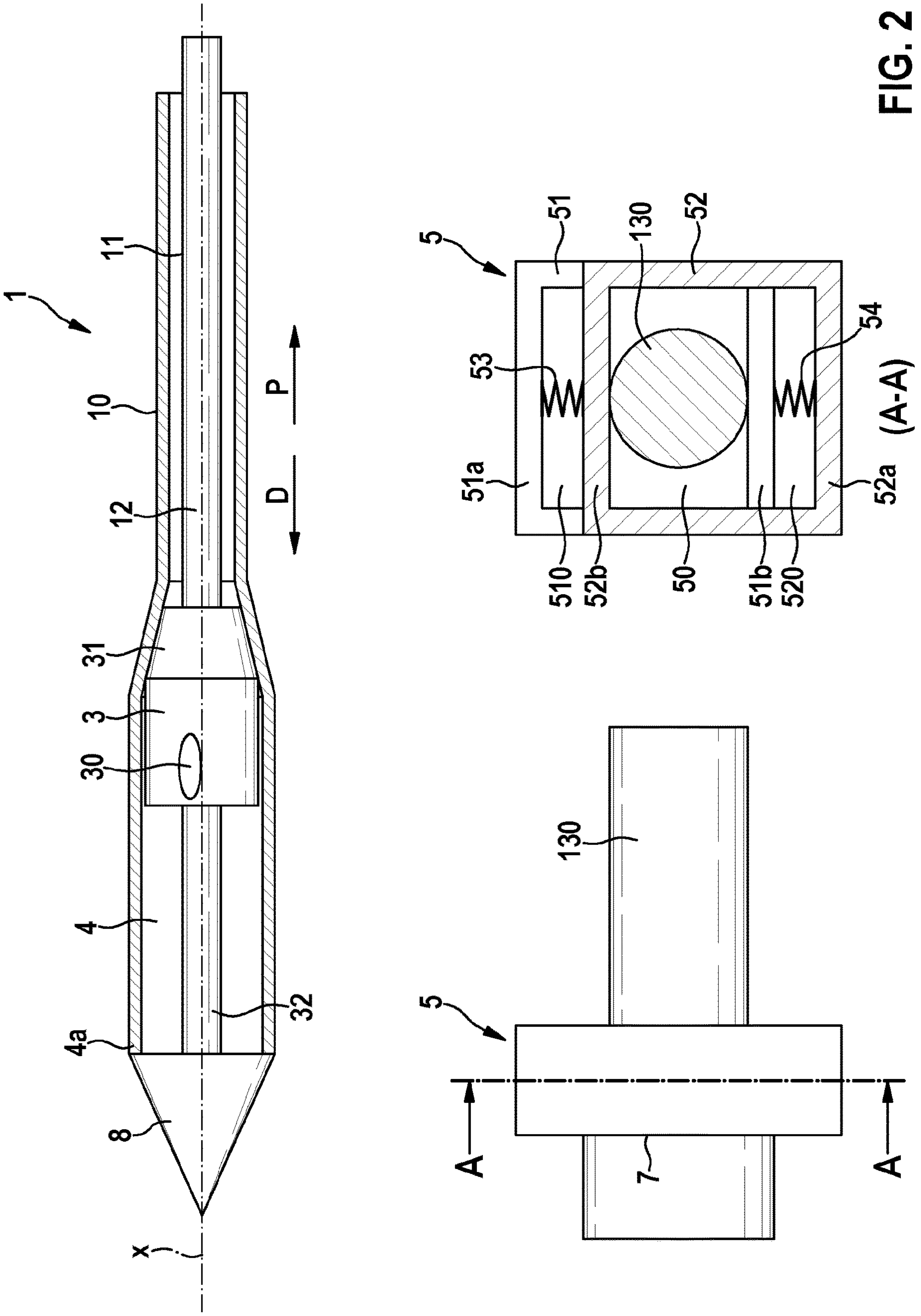
FIGS. 2A-2C show the device of FIGS. 1A-1C, wherein the overstroke limit has been reached so that the capsule contacts a capsule stop connected to the inner sheath and an end of the capsule contacts a catheter tip of the device.

In particular, the catheter device 1/capsule 4 is closed when the distal end 4*a* of the capsule 4 touches a proximal portion of the catheter tip 8 which corresponds to the position when the actuating element 5 touches the first stop 7 (see FIGS. 2A-2C). A special configuration here is that additionally the capsule stop 31 and the capsule 4 meet at this position as well.

As indicated in FIGS. 1A to 4, the actuating element 5 can include two first portions 51*a*, 52*a* that form buttons 51*a*, 52*a* (so called "safety buttons") which can be assembled in a mirror symmetrical fashion. The overlap between two movable annular members 51, 52 forming the two buttons 51*a*, 52*a* creates a through-opening 50 where a handle core 130 of a handle 13 of the catheter device 1 can be guided through. The two buttons 51*a*, 52*a* can be spring loaded so that they are always sitting tight on a surface of the handle (for example of the rotatable member 131) corresponding to a first state of the actuating element 5. When the actuating element 5 butts against the first stop 7 the buttons 51*a*, 52*a* can be pushed towards one another to increase the inner diameter of the through-opening 50 (second state of the actuating element 5), so that they can travel over the larger outer diameter of the first stop 7 formed on the handle core 130 (see FIG. 4).

As shown in FIGS. 1A to 4 and also FIGS. 10A to 12B, each of the two movable members 51, 52 that are arranged side-by-side to create the through-opening 50 as overlap between the individual openings 510, 520 of the respective member 51, 52 also includes a second portion 51*b*, 52*b*, opposing the respective first portion 51*a*, 52*a*.

In this regard, the two movable members 51, 52 of the actuating element 5 are positioned with respect to one another, such that the first portion 51*a* of the first movable member 51 faces the second portion 52*b* of the second movable member 52, and such that the second portion 51*b* of the first movable member 51 faces the first portion 52*a* of the second movable member 52 (in FIGS. 10A to 12B the members 51, 52 are displayed individually and are not arranged side-by-side).

Figure 4:
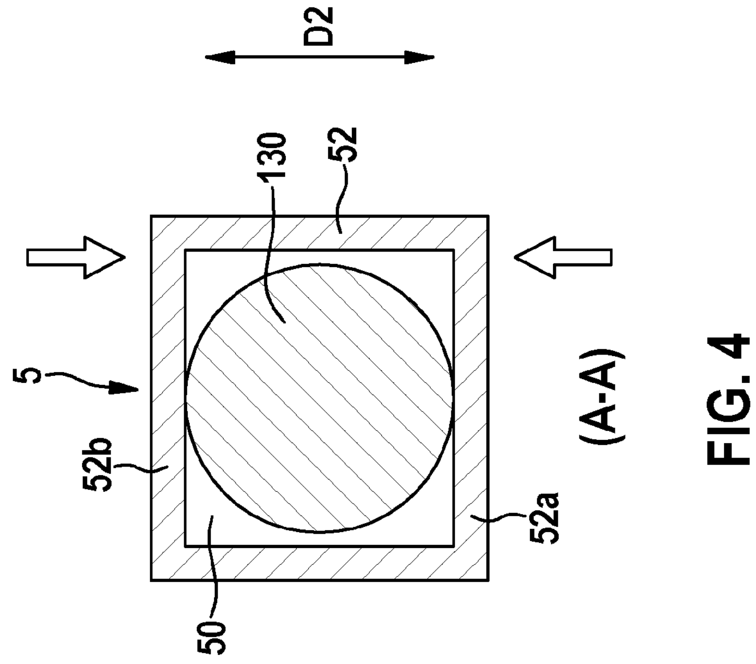
FIG. 4 shows the actuating element of FIG. 3 in the second state, wherein the actuating element has an enlarged inner diameter and can therefor pass the stop(s) of the catheter device.
Figure 3:
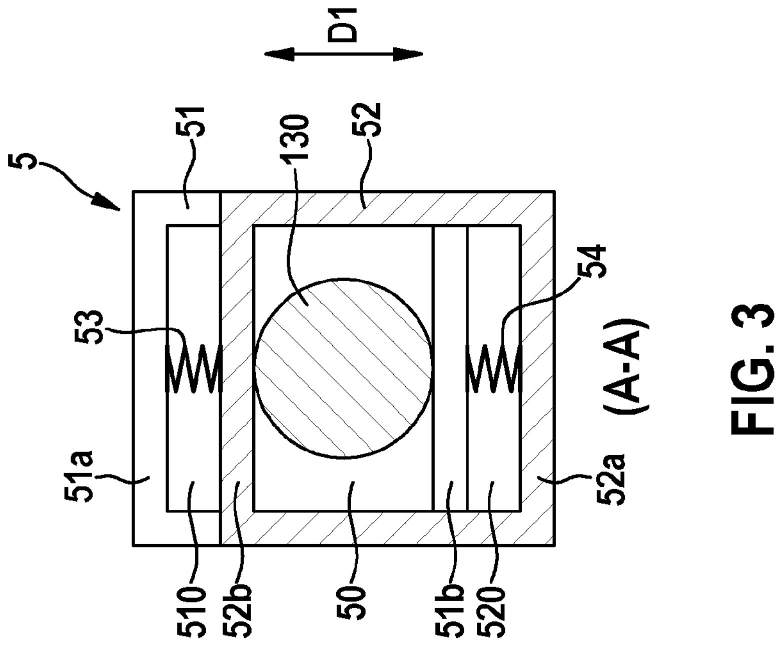
FIG. 3 shows a schematical plan view of the actuating element shown in FIGS. 1A-1C and 2A-2C, wherein the actuating element is in the first state and thus able to engage with a stop of the catheter device to provide, e.g., an overstroke limit.

For forcing the movable members 51, 52 to assume first positions corresponding to a smaller inner diameter D1 of the through-hole 50 (first state of the actuating element 5), cf., e.g., FIGS. 3 and 4, the actuating element 5 includes a first spring 53 (e.g. a coil spring) arranged between the first portion 51*a* of the first movable member 51 and the second portion 52*b* of the second movable member 52, and a second spring 54 (e.g. a coil spring) arranged between the first portion 52*a* of the second movable member 52 and the second portion 51*b* of the first movable member 51, so that the two first portions 51*a*, 52*a* that form the pushable buttons 51*a*, 52*a* of the actuating element 5 can be manually pushed towards one another to move each of the two movable members 51, 52 from its first position to a second position against a restoring force generated by the first and the second spring 53, 54. In the second positions (cf. FIG. 4) corresponding to the second state of the actuating element 5, the actuating element's through-opening 50 includes the larger inner diameter D2 that allows the actuating element 5 to pass the first stop 7 (or second stop 6 described further below). The springs 53, 54 may also be formed by a rubber element, respectively, or by an extrusion having a high elasticity.

Figure 5:
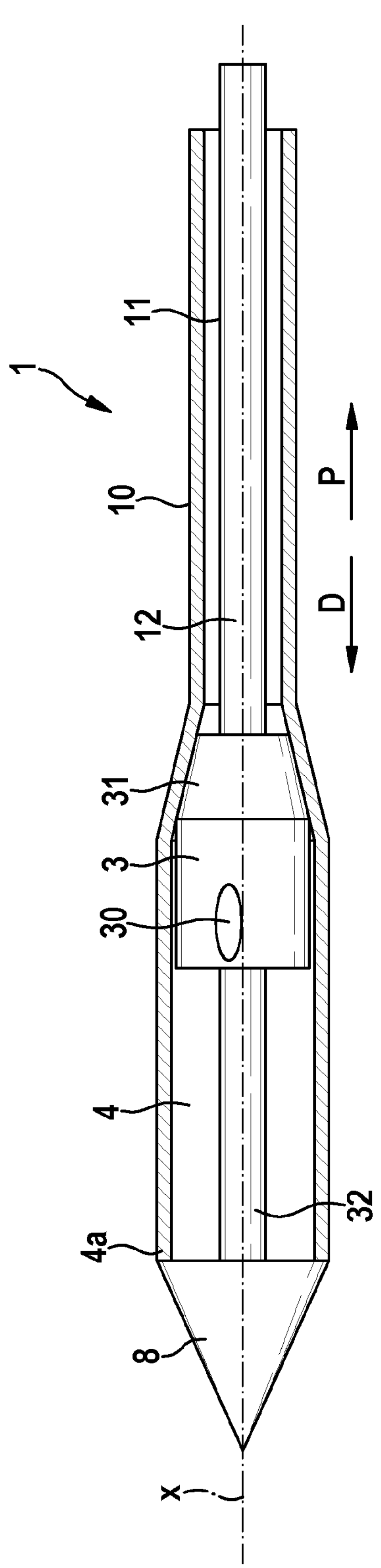
FIGS. 5A-5C show the device of FIGS. 1A-1C and 2A-2C, wherein here the actuating element is exemplarily moved in the distal direction past the stop defining the overstroke limit, so that the inner and outer sheaths are stressed.
Figure 5:
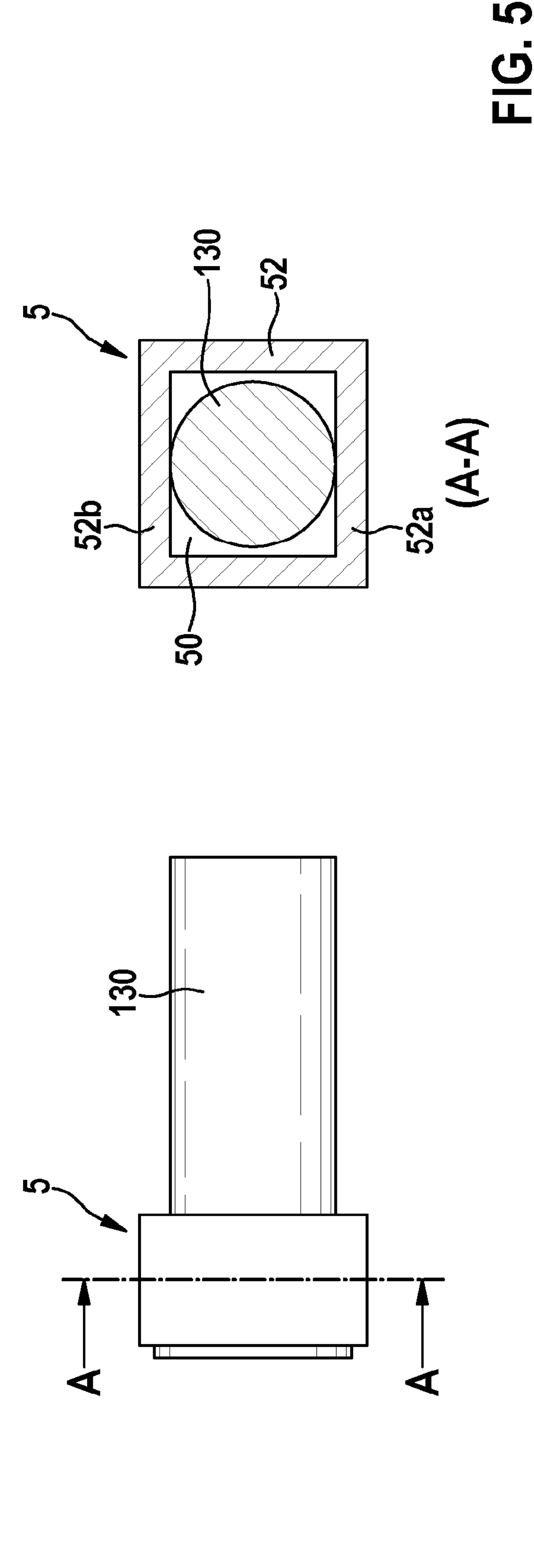

A shown in FIGS. 5A-5C, a manipulation of the actuating element 5 (for example pushing the buttons 51*a*, 52*a* in the embodiment described above) allows the actuating element 5 to overcome the overstroke limit/first stop 7. In this configuration the distal end 4*a* of the capsule 4 is not moved over the catheter tip 8 due to the capsule stop 31 but a mechanical load is introduced into the sheaths 10, 12.

Figure 6:
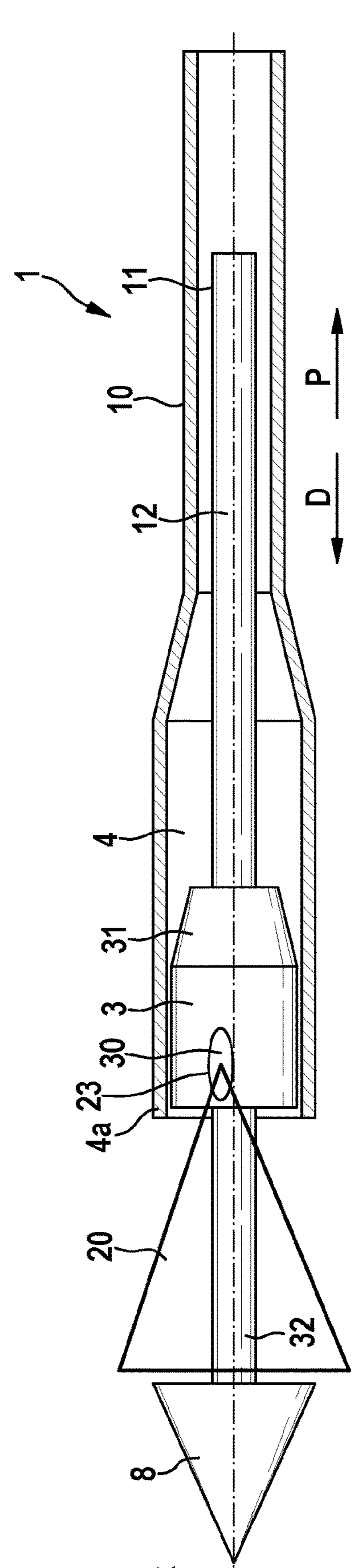
FIGS. 6A-6C show a further embodiment of a catheter device according to the present invention including a first and a second stop providing an overstroke limit and a re-sheathing limit, wherein the re-sheathing limit is reached and no further movement of the capsule in the exemplarily proximal direction is possible without releasing the medical implant.
Figure 6:
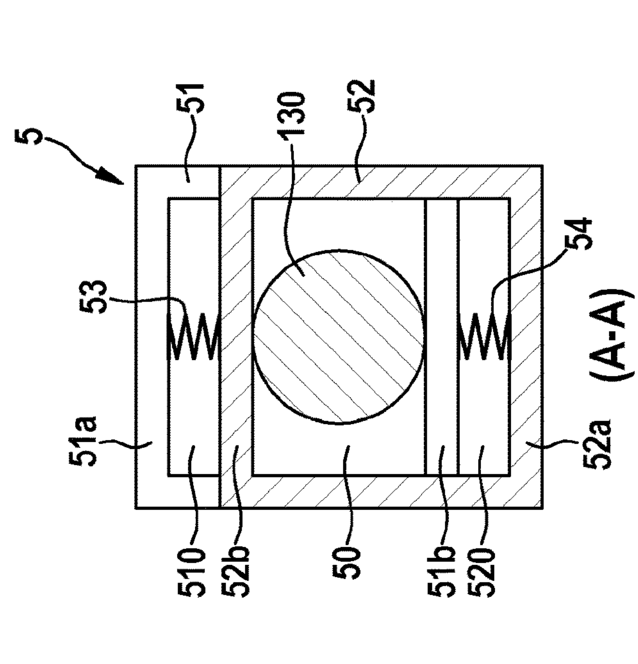
Figure 6:
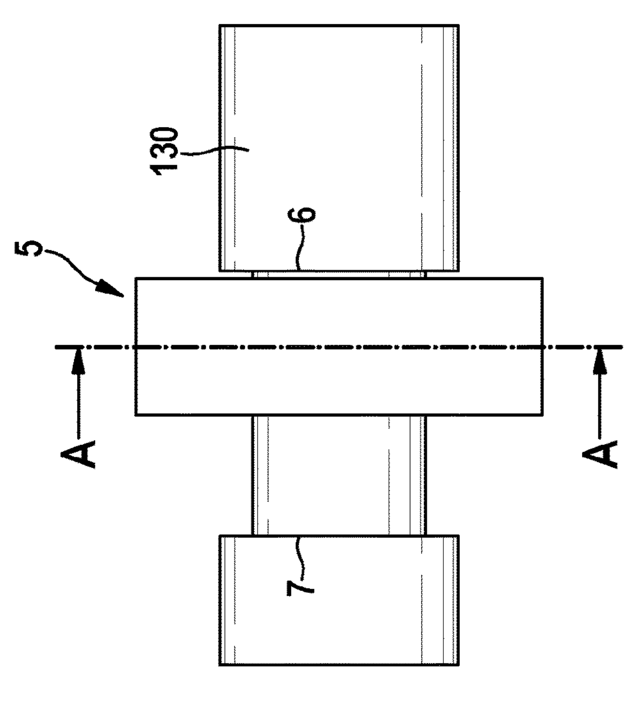

Furthermore, using a second stop 6, a limiter for the maximal deployment of the implant 2 (cf., e.g., FIG. 7D) until the point of no return which is commonly termed "re-sheathing limit" can be created with the same principle (see e.g. FIGS. 6A-6C). Until this point/limit the implant 2 can be re-sheathed, i.e. the capsule 4 can be completely moved over the partially deployed implant 2 for another deployment attempt or for a withdrawal of the implant 2.

A re-sheathing limit identifies when inner and outer sheaths 12, 10 are in a defined position with respect to each other. An actuating element 5 can be moved on the catheter device handle 13 and defines the relative position between inner and outer sheaths/shafts 12, 10. In case the actuating element 5 reaches the re-sheathing limit no further movement/deployment of the implant is possible. At this position the prosthesis connector 3 is still inside the implant capsule 4 and the implant's fastening elements 23 (e.g. eyelets) are still connected (see FIGS. 6, 7A) to the connector 3.

As shown in FIGS. 6A-6C, a second stop 6 can be used to realize the re-sheathing limit, wherein this second stop 6 is adapted to limit a movement of the actuating element 5 and therewith of the capsule 4 exemplarily in the proximal direction P when the actuating element 5 is in the first state, so as to prevent release of the medical implant 2 from the connector 3, and configured to allow movement of the actuating element 5 past the second stop 6 when the actuating element 5 is in the second state, so as to allow complete deployment and release of the medical implant 2 from the connector 3.

Particularly, as shown in FIGS. 6A-6C in conjunction with FIG. 7D, for allowing partial deployment of the medical implant 2 and optional re-sheathing of the medical implant 2, the capsule 4 includes a section (for example a distal end section 4*a*) that is configured to cover fastening elements 23 (e.g. eyelets) of the implant 2 engaged with recesses 30 of the connector 3 when the actuating element 5 contacts the second stop 6. Particularly, the fastening elements 23 can be connected to a stent 20 of the implant 2 that carries an artificial valve 21 (e.g. out of a biological tissue) including leaflets 23.

In case the capsule 4 is now moved completely away from the fastening elements 23 arranged in corresponding recesses 30 of the connector 3, so that said section 4*a* of the capsule 4 no longer covers the fastening elements 23, the fastening elements 23 are set free and automatically disengage from the recesses 30 of the connector 3 and medical implant 2 assumes its fully deployed state. This automatic disengagement can be generated by a self-expanding property of the medical implant 2/particularly of the stent 2, wherein the fastening elements 23 move away from the connector 3 and disengage the connector 3 due to said self-expanding property, once the capsule 4 (particularly said section 4*a* of the capsule 4) no longer covers the fastening elements 23 and thus no longer holds them in a fixed position with respect to the connector 3.

Full deployment and release of the implant 2 can be achieved by bringing the actuating element 5 from the first state to the second state, so that its through-opening 50 includes the larger second inner diameter D2 which allows to move the actuating element 5 past the second stop 6 exemplarily in the proximal direction P as shown in FIGS. 7A-7C.

Figures 8, 9:
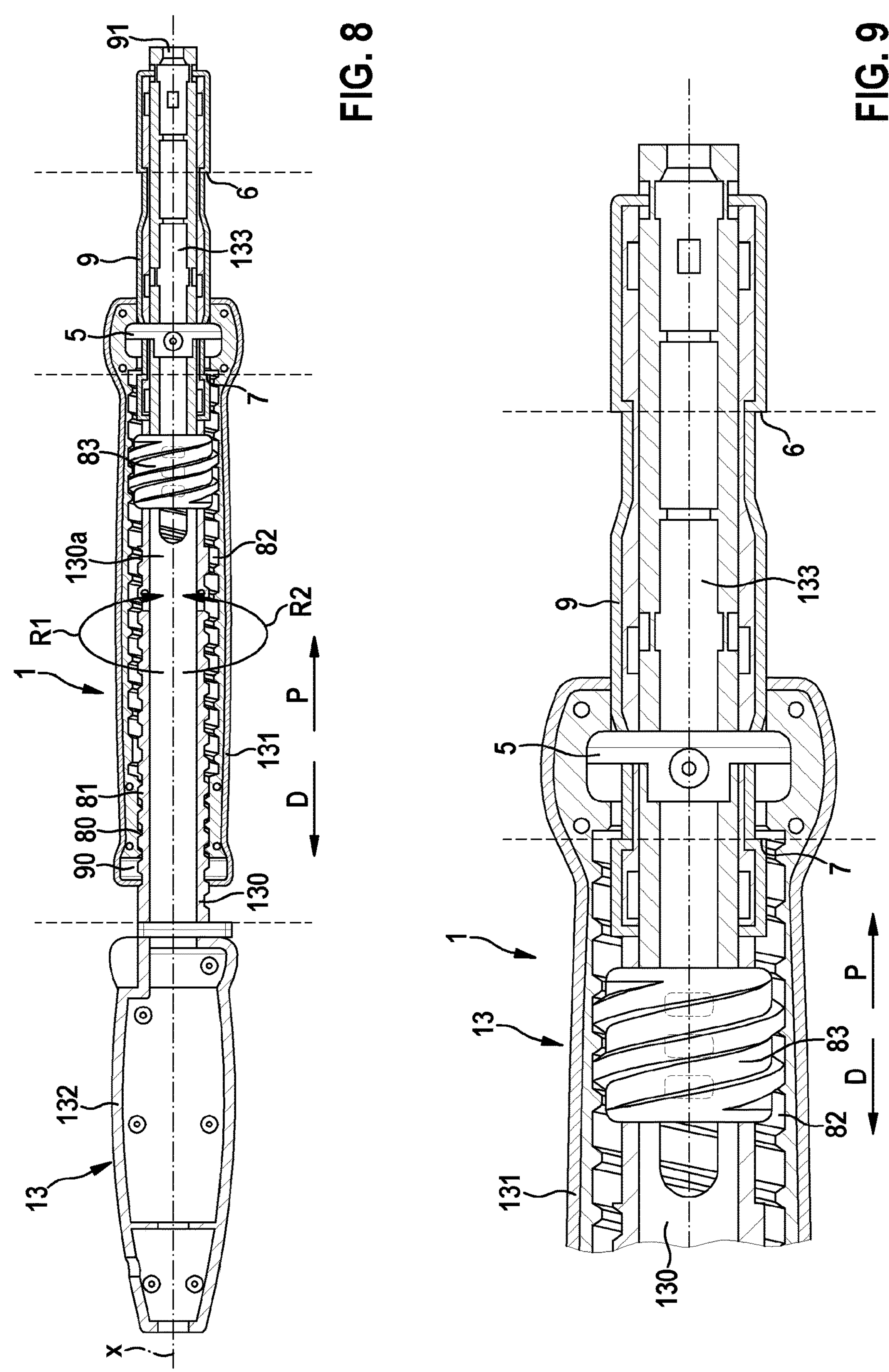
FIG. 8 shows a handle of an embodiment of a catheter device according to the present invention including a first stop defining an overstroke limit, a second stop defining a re-sheathing limit and an actuating element including buttons for passing the respective limit.
FIG. 9 shows a detail of the handle shown in FIG. 8.
Figure 10:
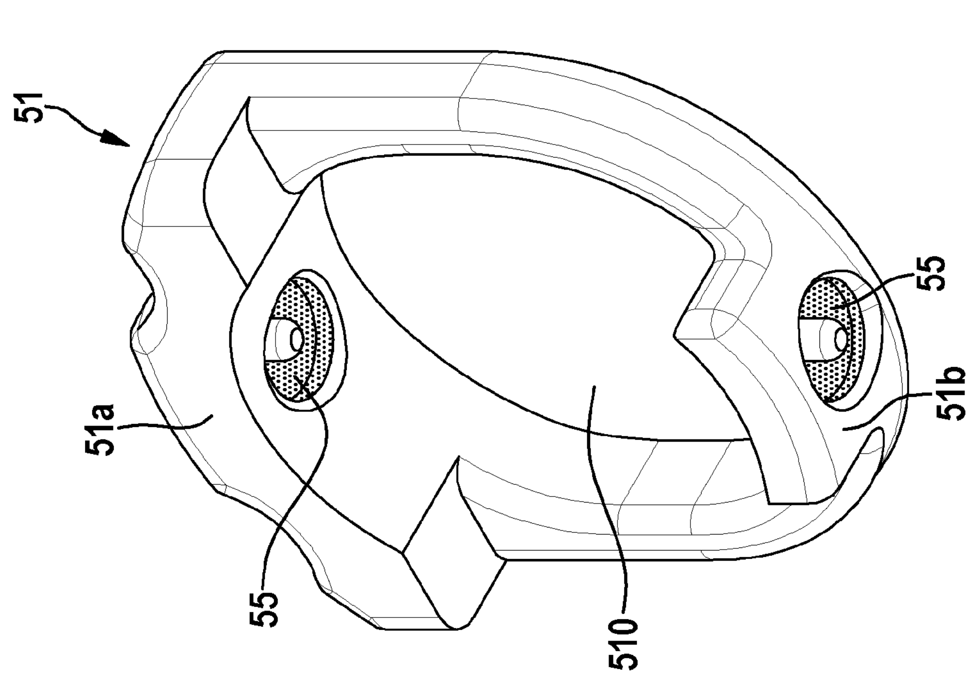
FIGS. 10A-10B show an embodiment of an actuating element of the catheter device according to the present invention.
Figure 10:
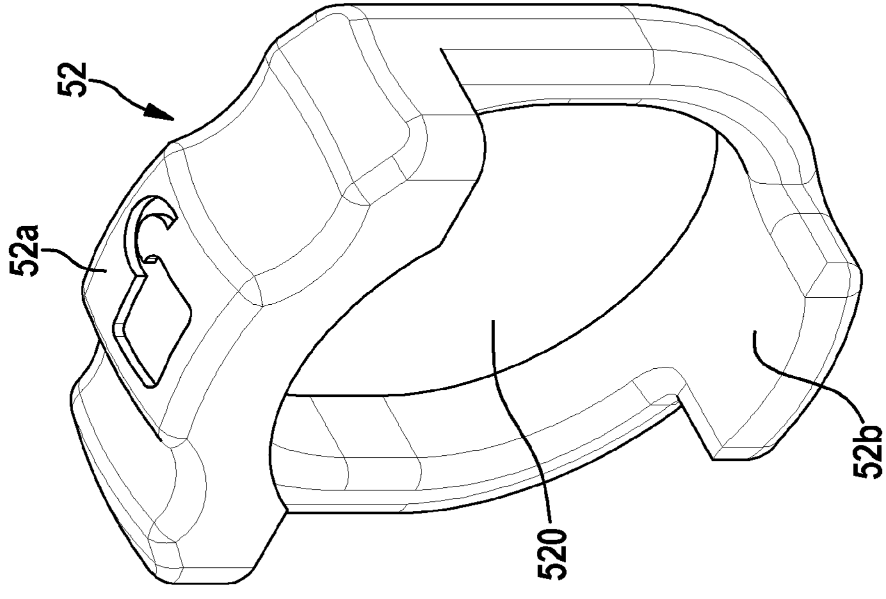

FIG. 8 shows a detail of an embodiment of the catheter device 1 according to the present invention, wherein a first stop 7 and a second stop 6 for providing an overstroke limit and a re-sheathing limit as well as an actuating element 5 for engaging the stops 6, 7 are provided on a handle 13 of the catheter device 1, which handle 13 is adapted for moving the capsule 4.

As shown in FIG. 8, the handle 13 includes a handle core 130 and a rotatable member 131 arranged on the handle core 130, wherein the rotatable member 131 is operatively connected to the capsule 4 via the outer sheath 10 such that the capsule 4 is exemplarily moved in the proximal direction P and is thereby withdrawn from the medical implant 2 when the rotatable member 131 is rotated in a first rotation direction R1, and such that the capsule 4 is moved back in the distal direction D to re-sheath the medical implant 2 when the rotatable member 131 is rotated in an opposite second rotation direction R2.

To engage/pass the stops 6, 7, the actuating element 5 is arranged on the rotatable member 131, wherein the buttons 51*a*, 52*a* of the actuating element 5 are accessible via corresponding openings in the rotatable member 131, so that they can be manually pushed to bring the actuating element 5 from the first state to the second state (e.g. against the actions of the springs 53, 53). Furthermore, the handle core 130 extends through the through-opening 50 of the actuating element 5.

The outer sheath 10 is not indicated in FIG. 8 but is connected to the rotatable member 131 at a connecting region 90 (e.g. via a bearing).

Furthermore, the handle 13 preferably includes a static grip portion 132 for manually holding the handle 13, wherein the grip portion 132 is connected to handle core 130.

Particularly, the second stop 6 is arranged on the handle core 130 and can be formed as a protrusion of the handle core 130, wherein the actuating element 5 is configured to hit the second stop 6 when the capsule 4 is exemplarily moved in the proximal direction P and the actuating element 5 is in the first state (i.e. includes smaller inner diameter D1), and wherein the actuating element 5 is allowed to move past the second stop 6 in the proximal direction P when the capsule 4 is moved in the proximal direction P and the actuating element 5 is in the second state (i.e. includes a larger inner diameter D2).

As described before, the capsule 4 is operatively connected to the rotatable member 131 such that the implant 2 is in a partially deployed state when the actuating element 5 hits the second stop 6 (re-sheathing limit) and is re-sheathable by rotating the rotatable member 131 in the second rotation direction R2, and such that the medical implant 2 is completely deployed and released from the connector 3 when the actuating element 5 is moved past the second stop 6 exemplarily in the proximal direction P.

Preferably, also the first stop 7 is arranged on the handle core 130 and can be formed as a protrusion of the handle core 130, wherein the actuating element 5 is configured to hit the second stop 7 when the capsule 4 is exemplarily moved in the distal direction D and the actuating element 5 is in the first state (i.e. includes a smaller inner diameter D1), and wherein the actuating element 5 is allowed to move past the second stop 7 in the distal direction D when the capsule 4 is moved in the distal direction D and the actuating element 5 is in the second state (i.e. includes a larger inner diameter D2).

Regarding the overstroke limit 7, the capsule 4 is operatively connected to the rotatable member 131 such that a distal end 4*a* of the capsule 4 contacts the catheter tip 8 and the capsule 4 completely covers the medical implant 2 when the actuating element 5 hits the second stop 7 (cf. FIG. 2), and such that the capsule 4 is pressed against the catheter tip 8 and/or against the capsule stop 31 when the actuating element 5 is moved past the second stop 7 exemplarily in the distal direction D (cf. FIGS. 5A-5C).

Particularly, for moving the capsule 4 using rotation of the rotatable member 131, the capsule 4 is connected to the rotatable member 131 via the outer sheath/shaft 10 (and connecting region 90), wherein the rotatable member 131 includes a first inner thread 80 engaging with an outer thread 81 formed on the handle core 130 such that the rotatable member 131 is moved in the proximal direction P together with the capsule 4 when it is rotated in the first rotation direction R1 and such that it is moved in the distal direction D together with the capsule 4 when it is rotated in the second rotation direction R2 (cf. FIG. 8).

To also move the inner sheath 12, the catheter device 1 can include according to FIGS. 8 and 9 a traveler 133 to which the inner sheath 12 is connected (e.g. at a proximal connecting region 91), wherein the inner sheath 12 in turn is connected to the connector 3 (and thus to the implant 2 when the latter is still connected to the connector 3).

The traveler 133 is arranged in a lumen 130*a* of the handle core 130 and includes an outer thread 83 configured to engage with a second inner thread 82 of the rotatable member 131 such that the traveler 133 and therewith the connector 3 being connected to the inner sheath/shaft 12 is exemplarily moved in the distal direction D when the rotatable member 131 is rotated in the first rotation direction R1 and such that the traveler 133 and therewith the connector 3 is moved in the proximal direction P when the rotatable member 131 is rotated in the second rotation direction R2.

Furthermore, as e.g. indicated in FIG. 9, a bump 9 can be formed by the handle core 130 between the stops 6, 7 which is however not mandatory for the function of the limits 6, 7 but provides benefits during the manipulation of the rotatable member 131 during the procedure.

Particularly, due to said bump 9, when the rotatable member 131 of the handle 13 is at the overstroke limit 7, the buttons 51*a*, 52*a* of the actuating element 5 are elevated in comparison to the outer surface of the rotatable member 131. This gives the user/physician the impression that the actuating element 5 may be activated to provide overstroke travel distance, if needed.

During the deployment, the rotatable member 131 travels over the bump 9 of the handle core 130. When the buttons 51*a*, 52*a* are moving over the increased diameter of the bump 9 they have to expand the inner diameter between the two buttons 51*a*, 52*a*. As a result, the height of the buttons 51*a*, 52*a* in comparison to the rotatable member's surface is reduced. The buttons 51*a*, 52*a* are now at the same level of this surface and activation of the buttons 51*a*, 52*a* is thus not possible (neither consciously nor unconsciously).

When the rotatable member 131 reaches the re-sheathing limit 6, the buttons 51*a*, 52*a* are on a smaller outer diameter of the handle core 130 again. As a result, they decrease the inner diameter of the actuating element 5 and the buttons 51*a*, 52*a* are elevated above the outer surface of the rotatable member. This is an indicator for the user that an activation of the buttons 51*a*, 52*a* is feasible to overcome the re-sheathing limit 6 for the full implant/prosthesis release.

In general, the herein disclosed limiter function principle (limiter mechanisms) can be used for catheters with or without foreshortening compensation.

Particularly, FIGS. 10A-10B show the basic functional principle of the two movable members 51, 52 of an actuating element 5. As indicated in FIGS. 10A-10B, the first and second portions 51*a*, 52*b*; 52*a*, 51*b* of the movable members 51, 52 that face each other, preferably include circular grooves 55 to receive the ends of the respective spring 53, 54 (cf., e.g., FIG. 3) in a form-fitting manner.

To further improve guiding of the buttons 51*a*, 52*a* with respect to each other, so that they do not have a tendency to separate or tilt upon engaging a stop 6, 7, each movable member 51, 52 (see FIGS. 11A-11B and FIGS. 12A-12B) includes a flat guiding surface 61, 62, wherein the föat guiding surfaces 61, 62 are configured to slide along each other when the two movable members 51, 52 are moved from their respective first position to their respective second position. Furthermore, according to an embodiment, each of the two movable members 51, 52 includes a recess 71, 72 into which the guiding surface of the other movable member engages. In this way, the recesses 71, 72 prevent separation of the members 51, 52.

The present invention provides the significant advantage that an overstroke limit and/or a re-sheathing limit is consciously set and the user thereby becomes aware of the potential performance change and the user can decide as to whether allowing for a further movement of the respective components, if so desired. Additionally, the capsule stop avoids increase of the crossing profile or component damage as the relative movement is prohibited and stress is introduced into the sheaths only.

Following the above disclosure, the skilled artisan readily appreciates that different applications of the subject-matter of the invention is conceivable. Especially, with suitable catheter configurations where a self-expanding medical implant is released from a catheter including an inner shaft and an outer shaft with an implant receptacle and where the medical implant is anchored/connected on/to the inner shaft in such a way that it can be recaptured as long as the medical implant is only released up to a certain point and is only fully released as soon as a certain point is exceeded.

For instance, in case the medical implant is a covered stent or a stent graft where a repositionability is advantageous, a respective delivery catheter implementing the subject-matter of the invention can be of value to the skilled person.

Moreover, the subject-matter of the instant invention may be adapted for delivery of closure systems such as LAA, PFO, ASD, VSD, and the like, or for catheter-based delivery of an implantable Leadless Pacer or of an implantable pressure sensor.

Thus, with the context of the invention the medical implant itself does not necessarily have to be self-expanding, it just requires at least some sort of attaching/connecting means between the implant and a respective catheter, given that the implant is released when a certain point is exceeded.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

The invention claimed is:

1. A catheter device for implanting a medical implant, comprising:

a connector for holding the medical implant;

a capsule configured to cover the medical implant when the medical implant is arranged on the connector and to thereby prevent release of the medical implant from the connector, wherein the capsule is movable in a first direction (P) with respect to the medical implant for deploying the medical implant and for releasing the medical implant from the connector, wherein the capsule is movable in a second direction (D) for re-sheathing the medical implant before it is released from the connector;

an actuating element configured to move with the capsule and to be manually operated to bring the actuating element from a first state to a second state; and one or both of a first stop and second stop, wherein the first stop is configured to limit a movement of the actuating element and therewith of the capsule in the second direction (D) when the actuating element is in the first state, so as to prevent pressing of the capsule against a catheter tip of the catheter device and/or against a capsule stop of the catheter device, and is configured to allow movement of the actuating element past the first stop when the actuating element is in the second state, so as to press the capsule against the catheter tip and/or against the capsule stop;

the second stop is configured to limit a movement of the actuating element and therewith of the capsule in the first direction (P) when the actuating element is in the first state, so as to prevent release of the medical implant from the connector, and is configured to allow movement of the actuating element past the second stop when the actuating element is in the second state, so as to allow complete deployment and release of the medical implant from the connector.

2. The catheter device according to claim 1, comprising an outer sheath extending along a longitudinal axis (x) of the catheter device and surrounding a lumen of the outer sheath, wherein a distal end of the outer sheath is connected to the capsule, and wherein the catheter device further comprises an inner sheath extending along the longitudinal axis (x), wherein the inner sheath is arranged in the lumen of the outer sheath and connected to the connector.

3. The catheter device according to claim 1, comprising a handle for moving the capsule with respect to the medical implant, wherein the handle comprises a handle core and a rotatable member arranged on the handle core, wherein the rotatable member is operatively connected to the capsule such that the capsule is moved in the first direction (P) and thereby withdrawn from the medical implant when the rotatable member is rotated in a first rotation direction (R1), and such that the capsule is moved back in the second direction (D) to re-sheath the medical implant when the rotatable member is rotated in a second rotation direction (R2).

4. The catheter device according to claim 1, wherein the actuating element comprises a through-opening that comprises a first diameter (D1) in the first state of the actuating element and a larger second diameter (D2) in the second state of the actuating element, wherein the handle core extends through the through-opening.

5. The catheter device according to claim 3, wherein the second stop is arranged on the handle core, wherein the actuating element is configured to hit the second stop when the capsule is moved in the first direction (P) and the actuating element is in the first state, and wherein the actuating element is allowed to move past the second stop in the first direction (P) when the capsule is moved in the first direction (P) and the actuating element is in the second state.

6. The catheter device according to claim 3, wherein the capsule is operatively connected to the rotatable member such that the implant is in a partially deployed state when the actuating element hits the second stop and is re-sheathable by rotating the rotatable member in the second rotation direction (R2), and such that the medical implant is completely deployed and released from the connector when the actuating element is moved past the second stop in the first direction (P).

7. The catheter device according to claim 3, wherein the first stop is arranged on the handle core, wherein the actuating element is configured to hit the first stop when the capsule is moved in the second direction (D) and the actuating element is in the first state, and wherein the actuating element is allowed to move past the first stop in the second direction (D) when the capsule is moved in the second direction (D) and the actuating element is in the second state.

8. The catheter device according to claim 3, wherein the capsule is operatively connected to the rotatable member such that a distal end of the capsule contacts the catheter tip and the capsule completely covers the medical implant when the actuating element hits the first stop, and such that the capsule is pressed against the catheter tip and/or against the capsule stop when the actuating element is moved past the first stop in the second direction (D).

9. The catheter device according to claim 4, wherein the actuating element comprises a movable first member comprising a first opening, and a movable second member comprising a second opening, wherein the two movable members are arranged side-by-side, so that overlapping regions of the openings form the through-opening of the actuating element, and wherein each of the two movable members is configured to be manually moved from a first position to a second position, wherein, when the first and the second member reside in the respective first position, the actuating element is in the first state and the through-opening comprises the first diameter (D1), and wherein when the first and the second movable member reside in the respective second position, the actuating element is in the second state and the through-opening comprises the second diameter (D2).

10. The catheter device according to claim 9, wherein each of the two movable members comprises a first portion and an opposing second portion, wherein the respective first portion forms a manually pushable button, and wherein the two movable members are arranged such with respect to one another that the first portion of the first movable member faces the second portion of the second movable member, and such that the second portion of the first movable member faces the first portion of the second movable member.

11. The catheter device according to claim 10, comprising a first spring arranged between the first portion of the first movable member and the second portion of the second movable member, and a second spring arranged between the first portion of the second movable member and the second portion of the first movable member, so that the two first portions can be manually pushed towards one another to move each of the two movable members from its first position to its second position against a restoring force generated by the first and the second spring.

12. The catheter device according to claim 11, wherein the first portion of the first movable member comprises a recess receiving a first end of the first spring, and wherein the second portion of the second movable member comprises a recess receiving a second end of the first spring, and wherein the first portion of the second movable member comprises a recess receiving a first end of the second spring, and wherein the second portion of the first movable member comprises a recess receiving a second end of the second spring.

13. The catheter device according to claim 9, wherein each of the two movable members comprises a flat guiding surface, wherein the flat guiding surfaces are configured to slide along each other when the two movable members are moved from their respective first position to their respective second position.

14. The catheter device according to claim 2, wherein the capsule is connected to the rotatable member via the outer sheath, wherein the rotatable member comprises a first inner thread engaging with an outer thread formed on the handle core such that the rotatable member is moved in the first direction (P) together with the capsule when it is rotated in the first rotation direction (R1) and such that it is moved in the second direction (D) together with the capsule when it is rotated in the second rotation direction (R2).

15. The catheter device according to claim 2, comprising a traveler connected to the connector via the inner sheath, wherein the traveler is arranged in a lumen of the handle core and comprises an outer thread configured to engage with a second inner thread of the rotatable member such that the traveler and therewith the connector is moved in the second direction (D) when the rotatable member is rotated in the first rotation direction (R1) and such that the traveler and therewith the connector is moved in the first direction (P) when the rotatable member is rotated in the second rotation direction (R2).

* * * * *